United States Patent [19]

Sato

[11] Patent Number: 4,520,219

[45] Date of Patent: May 28, 1985

[54] PROCESS FOR THE PRODUCTION OF PSEUDOCUMENE OR DURENE

[75] Inventor: Haruhito Sato, Sodegaura, Japan

[73] Assignee: Idemitsu Kosan Company Limited, Tokyo, Japan

[21] Appl. No.: 532,261

[22] Filed: Sep. 14, 1983

[30] Foreign Application Priority Data

Sep. 24, 1982 [JP] Japan ................. 57-164999

[51] Int. Cl.$^3$ ............................. C07C 2/70
[52] U.S. Cl. ................... 585/462; 585/463; 585/464; 585/466; 585/467
[58] Field of Search ............ 585/462, 463, 464, 466, 585/467

[56] References Cited

U.S. PATENT DOCUMENTS

| | | | |
|---|---|---|---|
| 4,002,698 | 1/1977 | Kaeding | 585/466 |
| 4,069,268 | 1/1978 | Siskin et al. | 585/462 |
| 4,379,761 | 4/1983 | Olson et al. | 585/466 |
| 4,384,155 | 5/1983 | Chu | 585/466 |

*Primary Examiner*—Curtis R. Davis
*Attorney, Agent, or Firm*—Frishauf, Holtz, Goodman & Woodward

[57] ABSTRACT

A process for producing pseudocueme or durene is described, comprising methylating xylene by the use as a catalyst of at least one crystalline silicate selected from the group consisting of crystalline borosilicate, fluorine-containing crystalline borosilicate, fluorine-containing crystalline aluminosilicate, and fluorine-containing crystalline boroaluminosilicate. The specific crystalline silicate catalyst increases the conversion of xylene and the selectivity of pseudocumene or durene. The process of the invention can be performed either in one step or in two steps. The two-step reaction provides various industrial advantages, such as a high degree of utilization of the methylating agent and a great increase in the selectivity of the product.

16 Claims, 3 Drawing Figures

PROCESS FOR THE PRODUCTION OF PSEUDOCUMENE OR DURENE

BACKGROUND OF THE INVENTION

The present invention relates to a process for the production of pseudocumene or durene, and more particularly, to a process for efficiently producing pseudocumene or durene from xylene by the use of specific crystalline silicates as a catalyst.

As is well known, pseudocumene or durene is produced by a method using a Lewis acid catalyst such as $AlCl_3$ or a method using a liquid acid type catalyst, such as sulfuric acid. In the both methods, however, it is necessary to use anti-corrosion equipment and moreover the selectivity of the desired product is undesirably low. Moreover, the latter method has a disadvantage that the conversion of the starting material is very low. In order to improve such a low conversion, Japanese Patent Application Laid-Open No. 43930/74 has proposed a method in which trimethoxy borate is added. In this method, however, either of the conversion and selectivity are not yet sufficiently satisfactory.

SUMMARY OF THE INVENTION

As a result of extensive investigations to overcome the problems as described above, it has been found that pseudocumene or durene can be efficiently produced by using crystalline borosilicate, fluorine-containing crystalline borosilicate, fluorine-containing crystalline aluminosilicate, or fluorine-containing crystalline boroaluminosilicate as a catalyst.

The present invention relates to a process for producing pseudocumene or durene by methylating xylene in the presence of a catalyst, characterized in that the catalyst is at least one crystalline silicate selected from the group consisting of crystalline borosilicate, fluorine-containing crystalline borosilicate, fluorine-containing crystalline aluminosilicate, and fluorine-containing crystalline boroaluminosilicate.

BRIEF DESCRIPTION OF THE DRAWING

The FIGS. 1, 2, 3 show X-ray diffraction patterns of crystalline silicate obtained in Preparation Example 1, 2, 3 as described hereinafter, respectively. In the figures, $2\theta$ means the Bragg angle (degree).

DETAILED DESCRIPTION OF THE INVENTION

The crystalline silicate used as a catalyst in the process of the invention is: (1) crystalline borosilicate, (2) fluorine-containing crystalline borosilicate, (3) fluorine-containing crystalline aluminosilicate, or (4) fluorine-containing crystalline boroaluminosilicate. The crystalline silicates (2), (3), and (4) can be prepared by subjecting crystalline borosilicate, aluminosilicate and boroaluminosilicate compounds, respectively, to a fluorinating treatment.

These crystalline silicates have various properties. In the process of the invention, the crystalline silicate catalyst can be selected appropriately and optionally depending on, e.g., reaction conditions, the type of a methylating agent, and the desired product.

The crystalline silicates as used herein will hereinafter be explained in detail.

(1) Crystalline Borosilicate

Various types of crystalline borosilicate are available. In particular, those silicates in which the molar ratio of $SiO_2$ to $B_2O_3$ ($SiO_2/B_2O_3$) is at least 12, especially from 20 to 500 are usually preferred. Suitable examples are the crystalline borosilicates as described in Japanese Patent Application Laid-Open Nos. 55500/78, 7598/80, 84313/81, 123817/82, and 129820/82. The crystalline borosilicates as described above can be prepared by various procedures, and there is no special limitation to the method of preparation thereof.

A method of preparation as generally used comprises adding a silica source and a boron oxide source and, if desired, a crystallization agent, e.g., alkylammonium salts, to water to prepare an aqueous mixture, and then subjecting the aqueous mixture thus prepared to a hydrothermal reaction. Various compounds can be used as the silica source, including silica powder, silicic acid, colloidal silica, and dissolved silica. This dissolved silica includes water glass silicate and alkali metal silicates, all containing from 1 to 5 moles of silicon dioxide per mole of sodium oxide or potassium oxide. As the boron oxide source, metaboric acid, tetraboric acid, anhydrous boric acid, and borates, such as borax, as well as boric acid can be used. In performing the hydrothermal reaction of the aqueous mixture containing the silica and boron oxide sources, there is no special limitation to the reaction conditions; i.e., it is sufficient for the reaction to be performed under such conditions (temperature, pressure, and heating time) that permit the preparation of crystalline borosilicate. In general, the reaction is performed at a temperature of 120° to 250° C., preferably 150° to 200° C. for a period of 10 hours to 7 days, preferably 24 hours to 2 days under autogenous pressure. The pH of the reaction system in performing the hydrothermal reaction can be determined appropriately; it is usually adjusted to a range of from 8 to 11 and preferably to a range of from 9 to 10. It is preferred that a suitable amount of crystallization agent be added to the reaction system. Examples of such crystallization agents include tetraalkylammonium salts, such as tetrapropylammonium bromide, tetrabutylammonium bromide, and tetraethylammonium bromide.

The crystalline borosilicate as prepared by the above-described preparation method takes various crystal structures depending on the type and amount of each of the silica and boron oxide sources, the hydrothermal reaction conditions, the type of the crystallization agent, and so forth. In the process of the invention, any of such crystalline borosilicates can be used. Of these borosilicates, crystalline borosilicates in which the molar ratio of $SiO_2$ to $B_2O_3$ is at least 12 are preferred. Particularly preferred are those crystalline borosilicates in which the molar ratio of $SiO_2$ to $B_2O_3$ is from 20 to 500. In preparing the crystalline borosilicates as described above, it is sufficient for the silica and boron oxide sources to be added to the reaction system in such a manner that the ratio of the silica source to the boron oxide source is from 20:1 to 500:1 (calculated as the molar ratio of $SiO_2$ to $B_2O_3$). The crystalline borosilicate prepared as described above is usually in the form of powder. If desired, it can be molded after adding a binder, e.g., alumina sol.

(2) Fluorine-Containing Crystalline Borosilicate

The fluorine-containing crystalline borosilicate can be prepared by subjecting the crystalline borosilicate as prepared above to a fluorinating treatment. This fluorinating treatment can be performed in various manners; i.e., it is sufficient for the treatment to be performed so that fluorine is introduced in the crystalline borosilicate, resulting in the preparation of the fluorine-containing crystalline borosilicate. One of typical methods of introducing fluorine is to bring the crystalline borosilicate into contact with organofluoro compounds, e.g., furon gas, at a temperature of from 400° to 600° C. Another method is to contact the crystalline borosilicate with, a fluorine-containing solution e.g., hydrofluoric acid, sodium fluoride, boron trifluoride, and monofluoroacetic acid in a liquid phase. Examples of furon gases which can be used include Furon-11 ($CFCl_3$), Furon-12 ($CF_2Cl_2$), Furon-13 ($CF_3Cl$), Furon-21 ($CHFCl_2$), Furon-22 ($CHF_2Cl$), Furon-23 ($CHF_3$), Furon-113 ($CF_2ClCFCl_2$), and Furon-114 ($CF_2ClCF_2Cl$).

The fluorine-containing crystalline borosilicate can be prepared also by a method in which a fluorine source is added in combination with the silica and boron oxide sources to prepare an aqueous mixture, and the aqueous mixture is then subjected to the hydrothermal reaction. As the fluorine source, water-soluble compounds such as hydrofluoric acid and sodium fluoride are preferred.

The fluorine-containing crystalline borosilicate as prepared above is molded as such or after adding a suitable binder, e.g., aluminasol, and then calcined at a temperature of from 550° to 1,000° C. to prepare the catalyst as used herein.

(3) Fluorine-Containing Crystalline Aluminosilicate

The fluorine-containing crystalline aluminosilicate is generally prepared by subjecting crystalline aluminosilicate to a fluorinating treatment. Various crystalline aluminosilicates can be used. Typical examples are ZSM-5, ZSM-11, ZSM-12, ZSM-23, ZSM-35, ZSM-38, and ZSM-48.

These crystalline aluminosilicates can be prepared by various methods. Usually, they are prepared in the same manner as in the preparation of the crystalline borosilicate as described above except that an alumina source, e.g., aluminum sulfate, sodium alminate, colloidal alumina, and alumina, is used in place of the boron oxide source.

The fluorinating treatment can be applied in the same manner as in the case of the crystalline borosilicate as described above.

The fluorine-containing crystalline aluminosilicate thus prepared is molded in itself or after adding a suitable binder, e.g., aluminasol, and calcined at a temperature of 550° to 1,000° C. to prepare the catalyst as used herein.

(4) Fluorine-Containing Crystalline Boroaluminosilicate

The fluorine-containing crystalline boroaluminosilicate is generally prepared by subjecting crystalline boroaluminosilicate to the same fluorinating treatment as described in the preparation of fluorine-containing crystalline borosilicate. Various crystalline boroaluminosilicates are known, including those compounds as described in Japanese Patent Application Laid-Open No. 6752/80. These crystalline boroaluminosilicates can be prepared by various methods. Usually they are prepared in the same manner as in the preparation of the crystalline borosilicate as described above except that an alumina source is used in combination with the silica and boron oxide sources.

The crystalline boroaluminosilicate is then subjected to the same fluorinating treatment as described above to prepare the desired fluorine-containing boroaluminosilicate. The fluorine-containing boroaluminosilicate thus prepared is molded in itself or after adding a suitable binder, e.g., aluminasol, and then calcined at a temperature of from 550° to 1,000° C.

In the process of the invention, xylene (including p-xylene, o-xylene, m-xylene, and mixtures thereof) is used as a starting material, and is methylated using a methylating agent in the presence of the crystalline silicate catalyst (1), (2), (3) or (4) as described above to produce pseudocumene or durene.

Various compounds can be used as the methylating agent, including methanol, dimethyl ether, methyl chloride, and methyl bromide. Of these compounds, methanol and dimethyl ether are particularly preferred. The amount of the methylating agent used herein can be determined appropriately depending on the reaction conditions, the type of the desired product, and so forth. The molar ratio of the xylene to the methylating agent is usually from 20:1 to 1:20, preferably from 5:1 to 1:5, and more preferably from 2:1 to 1:4.

Other reaction conditions in carrying out the process of the invention are not critical. In general, the reaction temperature is from 200° to 700° C., preferably from 250° to 400° C., and especially preferably from 280° to 350° C.; the reaction pressure is from atmospheric pressure to 100 kilograms per square centimeter by gauge ($kg/cm^2G$) and preferably from atmospheric pressure to 10 kilograms per square centimeter by gauge ($kg/cm^2G$); and the liquid hourly space velocity (LHSV) is from 0.05 to 100 per hour and preferably from 0.1 to 10 per hour.

In the process of the invention, xylene is usually used as the starting material, but toluene can be used in place of or in combination with xylene. When, however, toluene is used as the starting material, crystalline borosilicate is not preferable as a catalyst since the selectivity of pseudocumene or durene is undesirably lowered. Therefore, when toluene is used as the starting material, fluorine-containing crystalline borosilicate, fluorine-containing crystalline aluminosilicate or fluorine-containing crystalline boroaluminosilicate is preferably used as a catalyst.

Moreover, in the process of the invention, pseudocumene can be used in place of xylene as the starting material. When pseudocumene is used as the starting material, the main product obtained by the process of the invention is durene. The methylation reaction in the process of the invention is usually carried out in one step. If it is carried out in two steps, the degree of utilization of the methylating agent increases and moreover it is possible to increase the selectivity of pseudocumene or durene.

The two-step reaction as described above usually comprises the first reaction step where xylene is methylated and the second reaction step where at least a part of the reaction mixture from the first reaction step is further methylated. This two-step reaction will hereinafter be explained in detail.

At the first reaction step, the production of pseudocumene from xylene is mainly conducted. Various methylating agents can be used for the first reaction step, including methanol and dimethyl ether. If only pseudocumene is desired to produce at the first reaction step, it is preferred to use a methylating agent composed mainly of dimethyl ether having a relatively low methylating ability.

After completion of the first reaction step, the reaction mixture from the first reaction step is sent to the second reaction step where it is further methylated. In this case, the entire reaction mixture may be introduced in the second reaction step, or after separation or removal of a part of light gases from the reaction mixture, the remainder may be introduced in the second reaction step. At the second reaction step, the reaction mixture as introduced above is further methylated. As in the first reaction step, various methylating agents, such as methanol and dimethyl ether, can be used at the second reaction step. At the second reaction step, the methylation reaction of pseudocumene produced at the first reaction step and unreacted xylene mainly proceeds. If durene, in particular, is desired to produce, it is preferred to use a methylating agent composed mainly of methanol having a relatively high methylating ability.

When the methylating agent composed mainly of methanol as described above is used at the second reaction step, the methylating agent recovered contains a relatively large amount of dimethyl ether. Thus, by using the recovered methylating agent as a methylating agent for the first reaction step, the methylating agent can be effectively utilized. Although only the methylating agent recovered from the second reaction step can be used for the first reaction step, it is also possible to supply the recovered methylating agent in combination with a fresh methylating agent.

In the process of the invention using the specific crystalline silicate as described above, the transmethylation reaction of the starting material and the product, and the decomposition of the methylating agent are inhibited; i.e., side-reactions are reduced. This will increase the conversion of xylene and the selectivity of pseudocumene or durene.

The crystalline silicate catalyst as used herein possesses a very long service life. Hence the process of the invention can be performed continuously for long periods of time while maintaining high catalytic activity.

In the process of the invention, any one of pseudocumene and durene can be produced or both the pseudocumene and durene can be produced in a desired ratio by appropriately selecting the reaction conditions and the reaction time. For example, if the reaction is performed under relatively moderate conditions or for a short period of time, the methylation does not proceed so much, resulting in the production of a large amount of pseudocumene, whereas if the reaction is performed under severe conditions or for a long period of time, the proportion of durene being produced increases.

If the process of the invention is performed in two steps and the methylating agent is recovered for re-use, the degree of utilization of the methylating agent (the ratio of the methylating agent used only in the methylation reaction to the methylating agent reacted in overall reaction) is high and the selectivity of pseudocumene or durene is greatly high compared with the one-step reaction.

Hence the process of the invention is very advantageous for the industrial production of pseudocumene or durene and is of high practical value.

The present invention is described in greater detail with reference to the following Examples and Comparative Examples.

PREPARATION EXAMPLE 1

Preparation of Crystalline Borosilicate

Solution A was prepared by adding 0.67 gram of boric acid, 17.68 grams of concentrated sulfuric acid, and 26.32 grams of tetrapropylammonium bromide to 250 milliliters of water, and Solution B was prepared by adding 211.1 grams of water glass (consisting of 28.95% by weight of silicon oxide, 9.40% by weight of sodium oxide, and 61.65% by weight of water) to 250 milliliters of water.

Solutions A and B were added dropwise simultaneously to a solution of 79.0 grams of sodium chloride dissolved in 122 milliliters of water at room temperature over 60 minutes. The mixture thus obtained was adjusted to pH 9.5 using sulfuric acid and placed in an autoclave where it was heated at 170° C. for 20 hours.

Figure 1:
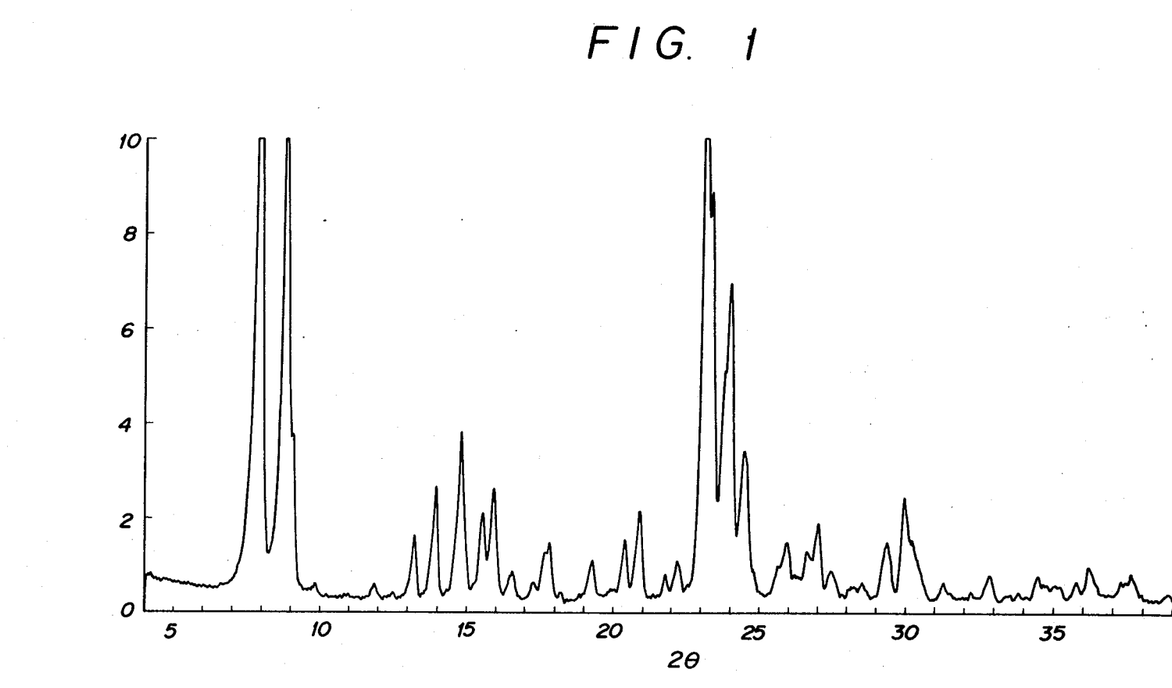

The contents of the autoclave was filtered while cooling and the solids thus obtained were washed with water. Then 300 milliliters of a 1 normal (N) aqueous solution of ammonium nitrate was added thereto and an ion exchange procedure was performed three times at 90° C. for 8 hours to obtain ammonium type crystalline borosilicate. The contents were then filtered and washed with water, dried at 120° C. for 24 hours, and calcined at 550° C. for 6 hours to obtain 58 grams of H type crystalline borosilicate ($SiO_2/B_2O_3 = 100/1$ (by mole)). Thus obtained crystalline borosilicate gave an X-ray diffraction pattern as shown in the FIG. 1.

To the H type crystalline borosilicate powder prepared above was added alumina sol as a binder so that the binder content was 20% by weight. The resulting mass was molded, dried at 120° C. for 3 hours, and then calcined in air at 550° C. for 6 hours to produce H type crystalline borosilicate pellets.

PREPARATION EXAMPLE 2

Preparation of Crystalline Aluminosilicate

Solution A was prepared by adding 6.2 grams of aluminum sulfate (18 hydrate), 17.68 grams of concentrated sulfuric acid, and 26.32 grams of tetrapropylammonium bromide to 250 milliliters of water, and Solution B was prepared by adding 211.1 grams of water glass (consisting of 28.95% by weight of silicon oxide, 9.40% by weight of sodium oxide, and 61.65% by weight of water) to 250 milliliters of water.

Solutions A and B were added dropwise simultaneously to a solution of 79.0 grams of sodium chloride in 122 milliliters of water at room temperature over 60 minutes. The mixture thus prepared was adjusted to pH 9.5 using sulfuric acid and placed in an autoclave where it was heated at a temperature of 170° C. for 20 hours.

Figure 2:
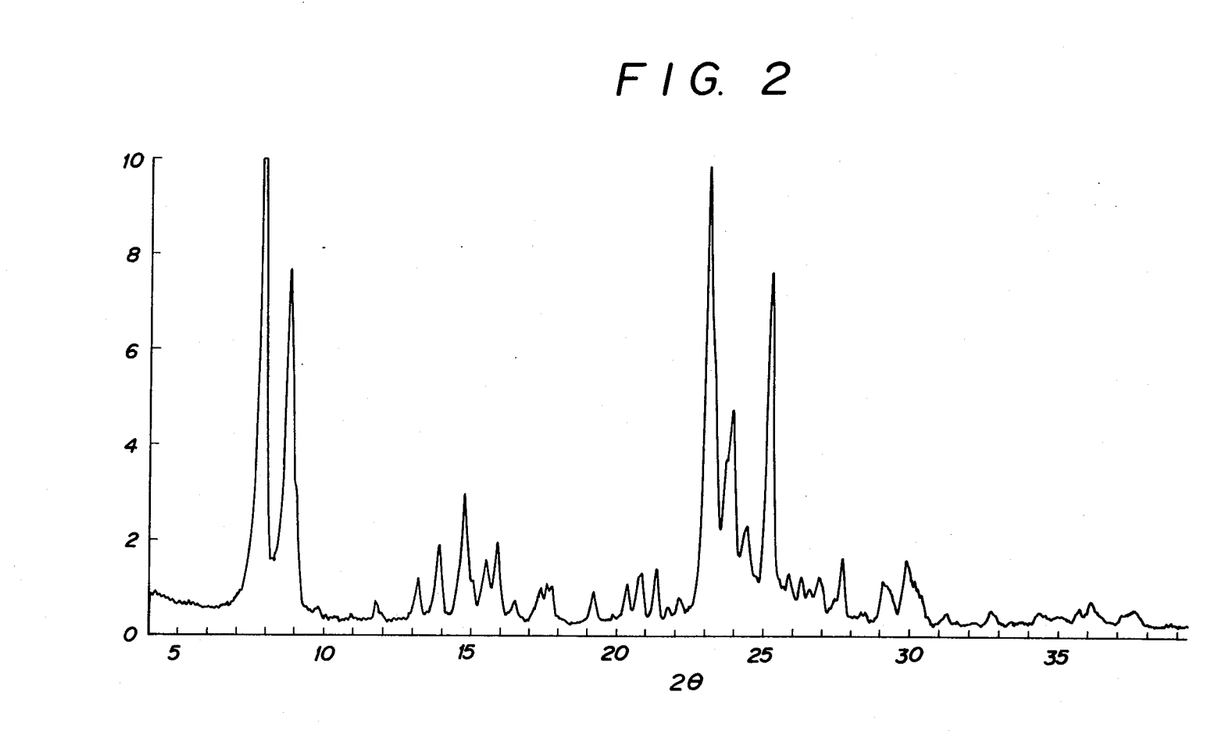

The contents of the autoclave was filtered while cooling and the solids thus obtained were washed with water. Then 300 milliliters of a 1 normal aqueous solution of ammonium nitrate was added thereto and an ion exchange procedure was performed three times at 90° C. for 8 hours to obtain ammonium type crystalline aluminosilicate. The contents were then filtered, washed with water, dried at 120° C. for 24 hours, and calcined at 550° C. for 6 hours to obtain H type crystalline aluminosilicate ($SiO_2/Al_2O_3 = 100/1$ (by mole)). Thus obtained crystalline aluminosilicate gave an X-ray diffraction pattern as shown in the FIG. 2.

To the H type crystalline aluminosilicate prepared above was added alumina sol as a binder so that the binder content was 20% by weight, and the resulting mass was molded, dried at 120° C. for 3 hours, and calcined in air at 550° C. for 6 hours to produce molded crystalline aluminosilicate zeolite (ZSM-5).

EXAMPLE 1

A flow type reactor was packed with H type crystalline borosilicate pellets prepared in Preparation Example 1, and a 1:4 (by mole) mixture of p-xylene and methyl alcohol was passed therethrough and reacted at a temperature of 330° C. under atmospheric pressure at a liquid hourly space velocity (LHSV) of 1 per hour. The conversion of xylene, the selectivity of the product, and so forth were measured after four hours from the start of the reaction. The results are shown in Table 1.

EXAMPLE 2

A reaction tube was packed with the crystalline aluminosilicate zeolite (ZSM-5) prepared in Preparation Example 2, and methyl alcohol was passed therethrought at 250° under atmospheric pressure at a liquid hourly space velocity (LHSV) of 1 per hour to produce dimethyl ether.

Then a 1:1 (by mole) mixture of dimethyl ether as prepared above and p-xylene was reacted by passing through a reaction tube packed with H type crystalline borosilicate pellets prepared in Preparation Example 1 at 330° C. under atmospheric pressure at a liquid hourly space velocity (LHSV) of 1 per hour. The conversion of p-xylene, the selectivity of the product, and so forth were measured after four hours from the start of the reaction. The results are shown in Table 1.

COMPARATIVE EXAMPLE 1

The reaction was performed in the same manner as in Example 1 except that H type aluminosilicate zeolite prepared in Preparation Example 2 was used in place of H type crystalline borosilicate. The results are shown in Table 1.

EXAMPLE 3

A catalyst preparation tube was packed with the crystalline borosilicate pellets as prepared in Preparation Example 1, and Furon-114 (1,1,2,2-tetrafluoro-1,2-dichloroethane) was supplied at a rate of 70 milliliters per minute for 1 hour to conduct a fluorinating treatment at 500° C. whereby fluorine-containing crystalline borosilicate was prepared.

The fluorine-containing crystalline borosilicate was placed in a flow type reactor, and a 1:4 (by mole) mixture of p-xylene and methyl alcohol was passed through the reactor where they were reacted at a temperature of 300° C. under atmospheric pressure at a liquid hourly space velocity (LHSV) of 1 per hour. Thus the methylation reaction of p-xylene was carried out to produce pseudocumene and durene. The conversion of p-xylene, the selectivity of the product, and so forth were measured after four hours from the start of the reaction. The results are shown in Table 1.

EXAMPLE 4

ZSM-5 prepared in Preparation Example 2 was fluorinated in the same manner as in Example 3 to prepare fluorine-containing ZSM-5. The methylation reaction of p-xylene was performed in the same manner as in Example 3 except that the fluorine-containing ZSM-5 prepared above was used in place of the fluorine-containing crystalline borosilicate. The conversion of p-xylene, the selectivity of the product, and so forth were measured after four hours from the start of the reaction. The results are shown in Table 1.

PREPARATION EXAMPLE 3

Preparation of Crystalline Boroaluminosilicate

Solution A was prepared by adding 3.35 grams of boric acid, 6.2 grams of aluminum sulfate (18 hydrate), 17.68 grams of concentrated sulfuric acid, and 26.32 grams of tetrapropylammonium bromide to 250 milliliters of water, and Solution B was prepared by adding 211.1 grams of water glass (consisting of 28.95% by weight of silicon oxide, 9.40% by weight of sodium oxide, and 61.65% by weight of water) to 250 milliliters of water.

Solutions A and B were added dropwise simultaneously to a solution of 79.0 grams of sodium chloride dissolved in 122 milliliters of water at room temperature over 60 minutes. The mixture thus prepared was adjusted to pH 9.5 using sulfuric acid and placed in an autoclave where it was heated at 170° C. for 20 hours.

Figure 3:
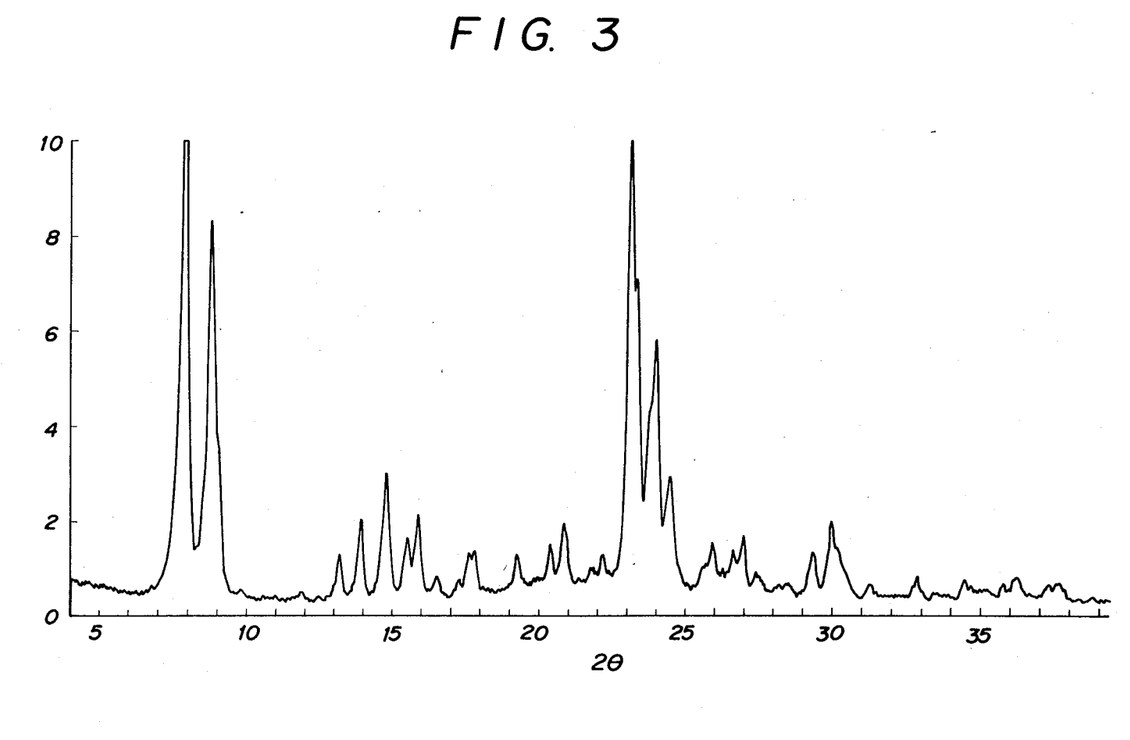

The contents of the autoclave was filtered while cooling and the solids thus obtained were washed with water. Then, 300 milliliters of a 1 normal aqueous solution of ammonium nitrate was added thereto and an ion exchange procedure was performed three times at 90° C. for 8 hours to obtain ammonium type crystalline boroaluminosilicate. The contents were then filtered, washed with water, dried at 120° C. for 24 hours, and then calcined at 550° C. for 6 hours to obtain 58 grams of H type crystalline boroaluminosilicate ($SiO_2/Al_2O_3/B_2O_3 = 100/1/5$ (by mole)). Thus obtained crystalline boroaluminosilicate gave an X-ray diffraction pattern as shown in the FIG. 3.

To the H type crystalline boroaluminosilicate powder prepared above was added alumina sol as a binder so that the binder content was 20% by weight. The resulting mass was molded, dried at 120° C. for 3 hours, and calcined in air at 550° C. for 6 hours to produce molded crystalline boroaluminosilicate.

EXAMPLE 5

The crystalline boroaluminosilicate as prepared in Preparation Example 3 was fluorinated in the same manner as in Example 3 to prepare fluorine-containing crystalline boroaluminosilicate. The methylation reaction of p-xylene was performed also in the same manner as in Example 3 except that the fluorine-containing crystalline boroaluminosilicate prepared above was used in place of the fluorine-containing crystalline borosilicate. The results as measured after four hours from the start of the reaction are shown in Table 1.

COMPARATIVE EXAMPLE 2

The procedure of Example 3 was repeated except that the crystalline boroaluminosilicate as prepared in Preparation Example 3 was used as such in place of the fluorine-containing crystalline borosilicate. The results as measured after four hours from the start of the reaction are shown in Table 1.

PREPARATION EXAMPLE 4

Preparation of Fluorine-Containing Crystalline Aluminosilicate

Solution A was prepared by dissolving 0.12 gram of sodium alminate (containing 35% by weight of $Al_2O_3$ and 30% by weight of $Na_2O$), 1.5 grams of sodium hydroxide, and 0.80 gram of ammonium fluoride in 185 milliliters of water, and furthermore by dissolving 14.2 grams of tetrapropylammonium bromide therein. Also, Solution B (38.0 grams) was prepared which was an aqueous solution of silica sol having a silica solid content of 30% by weight.

Solutions A and B were dropped simultaneously to 20 milliliters of water in a vessel at room temperature over 30 minutes. The mixture thus prepared was adjusted to pH 9.5 and placed in an autoclave where it was heated at 170° C. for 20 hours.

The contents of the autoclave was filtered while cooling. The solids thus obtained were washed with water. Then, 300 milliliters of a 1 normal aqueous solution of ammonium nitrate was added thereto and an ion exchange procedure was performed three times at 90° C. for 8 hours to obtain ammonium type fluorine-containing crystalline aluminosilicate. The contents were then filtered, washed with water, dried at 120° C. for 24 hours, and then calcined at 550° C. for 6 hours to produce H type fluorine-containing crystalline aluminosilicate.

To the fluorine-containing crystalline aluminosilicate prepared above was added alumina sol as a binder so that the binder content was 20% by weight. The resulting mass was molded, dried at 120° C. for 3 hours, and then calcined in air at 550° C. for 6 hours to produce molded fluorine-containing crystalline aluminosilicate.

EXAMPLE 6

The methylation reaction of p-xylene was performed in the same manner as in Example 3 except that the fluorine-containing crystalline aluminosilicate as prepared in Preparation Example 4 was used as a catalyst. The results as measured after four hours from the start of the reaction are shown in Table 1.

EXAMPLE 7

The methylation reaction was performed in the same manner as in Example 3 except that toluene was used as a starting material in place of p-xylene and that the reaction temperature was 330° C. in place of 300° C. The results as measured after four hours from the start of the reaction are shown in Table 1.

other through a cooler and a gas-liquid separator. Additionally, a cooler and a gas-liquid separator, and also a stripper through a reducing valve were connected to the outlet conduit of the second reactor, so that the stripper top gas could be liquified in the cooler and pumped to the first reactor.

A starting material, p-xylene, which had been heated previously was introduced in the first reactor maintained at 300° C. at a rate of 27 milliliters per hour, and methanol as a methylating agent was then introduced therein at a rate of 36 milliliters per hour. The methylation reaction of p-xylene was performed under a pressure of 9 kilograms per square centimeter by gauge ($kg/cm^2G$).

The reaction product from the first reactor was cooled to 30° C. in the cooler and sent to the gas-liquid separator where the gas component was separated. The obtained liquid component free from gas component was then introduced in the second reactor. In the second reactor, the temperature was 315° C. and the pressure was 9 kilograms per square centimeter ($kg/cm^2$). The reaction product from the second reactor was cooled to 30° C. in the cooler and sent to the gas-liquid separator where the gas component was separated and removed. The liquid component free from gas component was reduced in pressure to atmospheric pressure by means of the reducing valve and introduced in the stripper where it was again heated to 80° C. Dimethyl ether and unreacted methanol were withdrawn from the top of the stripper, liquified by cooling, and returned to the first reactor by means of the pump.

After the recycle of the unreacted methylating agent composed mainly of dimethyl ether was started, the introduction of methanol was changed from the first reactor to the second reactor. The liquid product obtained from the bottom of the stripper was treated to remove water therefrom and then distilled simply in a batch to produce pseudocumene and durene. After the recycle and re-use of the unreacted methylating agent from the second reactor reached a steady state, the composition of each of the products from the first and second reactors was measured. The results are shown in Table 2.

TABLE 1

|  | Example 1 | Examle 2 | Comparative Example 1 | Example 3 | Example 4 | Example 5 | Comparative Example 2 | Example 6 | Example 7 |
|---|---|---|---|---|---|---|---|---|---|
| Conversion of Xylene (%) | 43 | 41 | 45 | 42 | 63 | 42 | 44 | 56 | — |
| Conversion of Toluene (%) | — | — | — | — | — | — | — | — | 82 |
| Selectivity of Product (%) | | | | | | | | | |
| Pseudocumene | 59 | 60 | 38 | 69 | 61 | 78 | 51 | 63 | 22.3 |
| Durene | 39 | 36 | 33 | 30 | 38 | 21 | 23 | 35 | 8.1 |
| Other aromatic compounds | 2 | 4 | 29 | 1 | 1 | 1 | 26 | 2 | 5.3 |
| Pseudocumene Content (%)* | 96 | 95 | 67 | 99 | 100 | 100 | 87 | 98 | 89.9 |
| Durene Content (%)** | 93 | 93 | 74 | 98 | 100 | 100 | 65 | 97 | 74.3 |

Note:
*Pseudocumene (1,2,4-trimethylbenzene) content of aromatic hydrocarbons containing 9 carbons atoms.
**Durene (1,2,4,5-tetramethylbenzene) content of aromatic hydrocarbons containing 10 carbon atoms.

EXAMPLE 8

First and second reactors were each packed with 20 milliliters of the flourine-containing crystalline aluminosilicate pellets (ZSM-5 containing fluorine) as prepared in Example 4. These reactors were connected to each

TABLE 2

| | Product from First Reactor | Product from Second Reactor |
|---|---|---|
| Liquid Composition (% by weight) | | |
| Dimethyl ether | 6.4 | 12.2 |
| Methanol | 1.5 | 5.7 |
| $C_1$–$C_5$ Hydrocarbons | 0.8 | 1.0 |
| Benzene | 0.2 | 0.3 |
| Other $C_6$ hydrocarbons | 0.3 | 0.3 |
| Toluene | 0.3 | 0.3 |
| Ethylbenzene | 0 | 0.1 |
| Xylenes | 50.7 | 12.8 |
| Ethyltoluene | 0 | 0.1 |
| Pseudocumene | 22.1 | 17.0 |
| Other $C_9$ hydrocarbons | 0.1 | 0.3 |
| Durene | 7.4 | 20.5 |
| Other $C_{10}$ hydrocarbons | 0.1 | 0.4 |
| Water | 10.1 | 29.0 |
| Gas Composition (% by weight) | | |
| Methane | 1.0 | 1.5 |
| Ethylene | 56.9 | 59.8 |
| Ethane | 0.2 | 0.2 |
| Propylene | 36.1 | 29.9 |
| Propane | 1.6 | 3.4 |
| Dimethyl ether | 4.2 | 5.2 |

What is claimed is:

1. A process for producing at least one of pseudocumene and durene comprising reacting xylene and a methylating agent in the presence of a catalyst, which is at least one crystalline silicate selected from the group consisting of crystalline borosilicate, fluorine-containing crystalline borosilicate, fluorine-containing crystalline aluminosilicate, and fluorine-containing crystalline boroaluminosilicate;

said fluorine-containing crystalline borosilicate being prepared by contacting crystalline borosilicate with at least one fluorine-containing compound selected from the group consisting of HF, $NH_4F$, NaF, $BF_3$, $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$, said fluorine-containing crystalline aluminosilicate being prepared by contacting crystalline aluminosilicate with at least one fluorine-containing compound selected from the group consisting of HF, $NH_4F$, NaF, $BF_3$, $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$, and said fluorine-containing crystalline boroaluminosilicate being prepared by contacting crystalline boroaluminosilicate with at least one fluorine-containing compound selected from the group consisting of HF, $NH_4F$, NaF, $BF_3$, $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$.

2. The process of claim 1, wherein the methylating agent is selected from the group consisting of methanol, dimethyl ether, methylchloride and methylbromide.

3. The process of claim 2, wherein the methylating agent is methanol or dimethyl ether.

4. The process of claim 1, which comprises reacting xylene and a first methylating agent in the presence of said catalyst to thereby obtain a reaction mixture and reacting at least a part of the reaction mixture with a second methylating agent in the presence of said catalyst.

5. The process of claim 4, wherein said methylating agent is dimethyl ether and said second methylating agent is methanol.

6. The process of claim 4, further comprising recovering at least a portion of said second methylating agent.

7. The process of claim 6, further comprising employing said recovered methylating agent as said first methylating agent.

8. The process of claim 1, wherein the molar ratio of xylene to said methylating agent is 20:1 to 1:20.

9. The process of claim 8, wherein the molar ratio of xylene to said methylating agent is 5:1 to 1:5.

10. The process of claim 1, wherein said catalyst is selected from the group consisting of fluorine-containing crystalline borosilicate, fluorine-containing crystalline aluminosilicate and fluorine-containing crystalline boroaluminosilicate.

11. The process of claim 1, wherein said catalyst is crystalline borosilicate.

12. The process of claim 1, wherein the reaction is conducted at a temperature of 200° to 700° C. and a pressure of from atmospheric pressure to 100 kg/cm².G.

13. A process for producing pseudocumene or durene comprising reacting toluene and a methylating agent in the presence of a catalyst, which is at least one crystalline silicate selected from the group consisting of fluorine-containing crystalline borosilicate, fluorine-containing crystalline aluminosilicate, and fluorine-containing crystalline boroaluminosilicate;

said fluorine-containing crystalline borosilicate being prepared by contacting crystalline borosilicate with at least one fluorine-containing compound selected from the group consisting of HF, $NH_4F$, NaF, $BF_3$, $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$, said fluorine-containing crystalline aluminosilicate being prepared by contacting crystalline aluminosilicate with at least one fluorine-containing compound selected from the group consisting of HF, $NH_4F$, NaF, $BF_3$ $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$, and said fluorine-containing crystalline boroaluminosilicate being prepared by contacting crystalline boroaluminosilicate with at least one fluorine-containing compound selected from the group consisting of HF, $NH_4F$, NaF, $BF_3$, $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$.

14. A process for producing durene comprising reacting pseudocumene and a methylating agent in the presence of a catalyst which is at least one crystalline silicate selected from the group consisting of crystalline borosilicate, fluorine-containing borosilicate, fluorine-containing crystalline aluminosilicate, and fluorine-containing crystalline boroaluminosilicate;

said fluorine-containing crystalline borosilicate being prepared by contacting crystalline borosilicate with at least one fluorine-containing compound selected from the group consisting of HF, $NH_4F$, NaF, $BF_3$, $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$, said fluorine-containing crystalline aluminosilicate being prepared by contacting crystalline aluminosilicate with at least one fluorine-containing compound selected from the group consisting of HF, $NH_4F$, NaF, $BF_3$, $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$, and said fluorine-containing crystalline boroaluminosilicate being prepared by contacting crystalline boroaluminosilicate with at least one fluorine-containing compound selected from the group consisting of HF, $NH_4F$, NaF, $BF_3$ $CFCl_3$, $CF_2Cl_2$, $CF_3Cl$, $CHFCl_2$, $CHF_2Cl$, $CHF_3$, $CF_2ClCFCl_2$ and $CF_2ClCF_2Cl$.

15. The process of claim 14, which comprises reacting xylene and a first methylating agent in the presence of said catalyst to thereby obtain a reaction mixture and reacting at least part of the reaction mixture with a second methylating agent in the presence of said catalyst.

16. The process of claim 15, wherein each of said first and second methylating agent is methanol.

* * * * *

Notice of Adverse Decision in Interference

In Interference No. 101,550, involving Patent No. 4,520,219, H. Sato, PROCESS FOR THE PRODUCTION OF PSEUDOCUMENE OR DURENE, final judgment adverse to the patentee was rendered Sept. 26, 1988, as to claims 1 - 16.

[*Official Gazette February 14, 1989.*]